US011446112B2

(12) United States Patent
Fink et al.

(10) Patent No.: US 11,446,112 B2
(45) Date of Patent: Sep. 20, 2022

(54) INJECTION SITE TARGETING DEVICE

(71) Applicant: Helios Medical Ventures LLC, Dallas, TX (US)

(72) Inventors: Ezekiel Fink, Dallas, TX (US); Robert E. Hanes, Manvel, TX (US); Joel Henry, Manvel, TX (US); Bruce Schroeder, Manvel, TX (US)

(73) Assignee: Helios Medical Ventures LLC, Dallas, TX (US)

( * ) Notice: Subject to any disclaimer, the term of this patent is extended or adjusted under 35 U.S.C. 154(b) by 616 days.

(21) Appl. No.: 16/071,159

(22) PCT Filed: Jan. 20, 2017

(86) PCT No.: PCT/US2017/014422
§ 371 (c)(1),
(2) Date: Jul. 19, 2018

(87) PCT Pub. No.: WO2017/127738
PCT Pub. Date: Jul. 27, 2017

(65) Prior Publication Data
US 2019/0231470 A1 Aug. 1, 2019

Related U.S. Application Data

(60) Provisional application No. 62/281,496, filed on Jan. 21, 2016.

(51) Int. Cl.
*A61M 5/142* (2006.01)
*A61B 90/11* (2016.01)
(Continued)

(52) U.S. Cl.
CPC ............ *A61B 90/11* (2016.02); *A61M 5/427* (2013.01); *A61B 2017/00862* (2013.01);
(Continued)

(58) Field of Classification Search
CPC .... A61M 5/427; A61B 90/11; A61B 17/3403; A61B 2017/3407; A61B 2017/3411
See application file for complete search history.

(56) References Cited

U.S. PATENT DOCUMENTS 4,593,698 A * 6/1986 Athans ................... A61B 5/107
600/386
6,007,549 A * 12/1999 Howard, III ........... A61B 90/11
602/74
(Continued)

FOREIGN PATENT DOCUMENTS

CN 101282690 10/2008
CN 201394079 2/2010
(Continued)

OTHER PUBLICATIONS

Levin, M. "Nerve Blocks in the Treatment of Headache" The Journal of the American Society for Experimental NeuroTherapeutics, Apr. 2010, pp. 197-203, vol. 7.
(Continued)

*Primary Examiner* — Laura A Bouchelle
(74) *Attorney, Agent, or Firm* — Larson & Anderson, LLC

(57) ABSTRACT

An apparatus for targeting an injection site using anatomical landmarks includes a first landmark identifier, a second landmark identifier, and a targeting band. The targeting band is connected with the first landmark identifier at a first end and a second landmark identifier at a second end. At least a portion of the targeting band is linearly deformable. In another embodiment, an apparatus for targeting an injection site using anatomical landmarks on a patient includes a targeting band having a first end and a second end, at least
(Continued)

a portion of the targeting being linearly deformable, a first landmark identifier pivotably connected to the targeting band at the first end, a second landmark identifier configured to be connected with the second end of the targeting band; and a fastener configured to secure the first and second landmark identifiers to the patient.

20 Claims, 17 Drawing Sheets

(51) Int. Cl.
    *A61M 5/42* (2006.01)
    *A61B 90/50* (2016.01)
    *A61B 17/34* (2006.01)
    *A61B 17/00* (2006.01)
    *A61B 90/00* (2016.01)
    *A61M 5/32* (2006.01)
    *A61B 90/10* (2016.01)

(52) U.S. Cl.
    CPC ............... *A61B 2017/00951* (2013.01); *A61B 2017/3407* (2013.01); *A61B 2017/3411* (2013.01); *A61B 2090/061* (2016.02); *A61B 2090/067* (2016.02); *A61B 2090/101* (2016.02); *A61B 2090/502* (2016.02); *A61M 5/3287* (2013.01)

(56) References Cited

U.S. PATENT DOCUMENTS

| | | | | |
|---|---|---|---|---|
| 7,122,038 | B2* | 10/2006 | Thomas | A61B 90/11 606/130 |
| 8,133,201 | B1* | 3/2012 | Hurtado | A61M 5/427 604/116 |
| 8,870,820 | B2* | 10/2014 | Murphy | A61M 5/427 604/116 |
| 8,989,836 | B2* | 3/2015 | Machon | A61B 5/316 600/383 |
| 2009/0299416 | A1 | 12/2009 | Hanni et al. | |
| 2012/0265138 | A1 | 10/2012 | Harylka et al. | |
| 2013/0327342 | A1 | 12/2013 | Watschke et al. | |
| 2015/0045732 | A1 | 2/2015 | Murphy et al. | |

FOREIGN PATENT DOCUMENTS

| | | |
|---|---|---|
| CN | 102107023 | 6/2011 |
| CN | 104 138 255 A | 11/2014 |
| EP | 2301454 A2 | 3/2011 |

OTHER PUBLICATIONS

Loukas, M. et al. "Identification of greater occipital nerve landmarks for the treatment of occipital neuralgia" Folia Morphol., 2006, pp. 337-342, vol. 65, No. 4.

Voigt, C. et al. "Occipital Nerve Blocks in the Treatment of Headaches: Safety and Efficacy", The Journal of Emergency Medicine, 2015, pp. 115-129, vol. 48, No. 1.

* cited by examiner

INJECTION SITE TARGETING DEVICE

CROSS-REFERENCE TO RELATED APPLICATIONS

This application claims the benefit of U.S. Provisional Patent Application No. 62/281,496, filed Jan. 21, 2016, the entire disclosure of which is incorporated by reference herein.

FIELD OF THE INVENTION

The present invention relates to an apparatus for targeting an injection site.

BACKGROUND

In medical procedures, it can be important to administer an injection or place a treatment device at a specific site on the body. Nerve blocks, for example, can be used to manage, treat, and prevent pain. The efficacy of a nerve block, however, depends largely upon the ability of a health care professional to correctly identify the relevant nerve(s) and the injection site(s) associated with the relevant nerve(s), and to administer the appropriate pharmaceuticals in close proximity to the identified nerve without encountering structures, such as blood vessels, that are hidden beneath the skin.

Nerves are typically located using anatomical landmarks, motor-evoked potential, or ultrasound. Each nerve-finding technique has advantages and drawbacks. However, they all generally require a significant amount of training beyond that of a general practitioner. Further, nerve finding via motor-evoked potential or ultrasound also requires costly equipment that requires additional training and may not be available in all clinical settings. Thus, there exists a need for a device that facilitates the administration of nerve blocks by eliminating the "guess work" associated with identifying injection sites. Further, the device increases the number of medical professionals, such as doctors of different specialties, and the like, that can administer nerve blocks in a clinical setting.

SUMMARY OF THE INVENTION

The present invention provides an apparatus for targeting an injection site using anatomical landmark guidance. In accordance with one embodiment of the present invention, an apparatus for targeting an injection site using anatomical landmarks includes a first landmark identifier, a second landmark identifier, and a targeting band connected with the first landmark identifier at a first end and the second landmark identifier at a second end. At least a portion of said targeting band is linearly deformable.

In accordance with another embodiment of the invention, an apparatus for targeting an injection site using anatomical landmarks on a patient includes a targeting band having a first end and a second end; a first landmark identifier pivotably connected to the targeting band at the first end; a second landmark identifier configured to be connected with the second end of the targeting band; and a fastener configured to secure the first and second landmark identifiers to the patient. At least a portion of the targeting is linearly deformable;

In accordance with another embodiment of the invention, an apparatus for targeting an injection site using anatomical landmarks on a patient, includes a first landmark identifier configured to be fixed to the patient; a pivot arm having a pivotable connection with the first landmark identifier; a targeting band having a first end and a second end, at least a portion of the targeting being linearly deformable, the first end of the targeting band being secured at the pivotable connection; and a second landmark identifier connected with the pivot arm.

In accordance with yet another embodiment of the invention, 22. An apparatus for targeting an injection site using anatomical landmarks on a patient includes a targeting band having a first end and a second end; a landmark identifier having directional markers thereon; and a tensioning member having a first end and a second end, the tensioning member being pivotably connected to the landmark identifier at the first end, the tensioning member comprising an adjustable tensioning mechanism configured to move between the first end and the second end, and a marker to indicate a targeted location. The first end of the targeting band is connected with the first end of the tensioning member and the second end of the targeting band is connected with the adjustable tensioning mechanism.

DETAILED DESCRIPTION

Figure 1A:
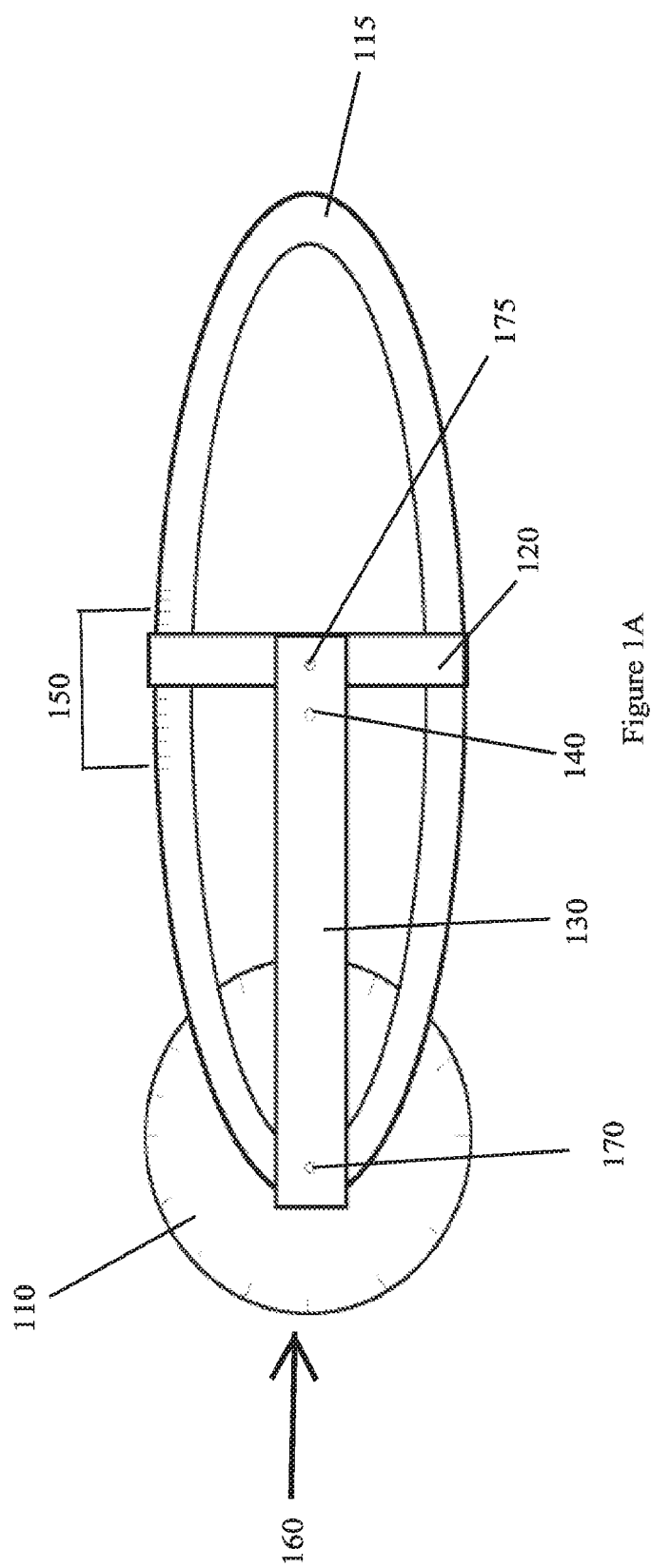
FIGS. 1A and 1B illustrate an injection site targeting device in accordance with the present invention.

Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and may or may not be present in other embodiments. In addition, it is to be understood that the described element(s) may be combined in any suitable manner in the various embodiments. Further, the term "user" herein describes an individual or group of individuals administering the injection. It should also be appreciated that the features disclosed herein may be combined in various ways without departing from the scope of the invention.

The location of underlying structures and/or tissues in the body such as nerves, tendons, muscles, vasculature, spine structures such as discs and facets, bones, joints and organs, etc. can sometimes be determined relative to anatomical landmarks that are identifiable via palpation or visual inspection. In some cases, the location of these underlying structures is well established via, for example, scientific study. For example, Levin identifies the location of the preferred injection site for a greater occipital nerve block as being located "approximately two thirds of the distance on a line drawn from the center of the mastoid to the external occipital protuberance." Levin, Morris. "Nerve Blocks in the Treatment of Headache." *Neurotherapeutics: The Journal of the American Society for Experimental NeuroTherapeutics* 7.1 (2010): 197-203, 198. Print. In some cases, literature suggests multiple approaches to locate a preferred injection site. Loukas, for example, suggests that the preferred injection site for a greater occipital nerve block is 2 cm lateral and 2 cm inferior to the greater occipital protuberance. Loukas, M., et al. "Identification of greater occipital nerve landmarks for the treatment of occipital neuralgia." *Folia Morphologica* 65.4 (2006): 337-342, 347. Print. Still other publications suggest multiple injection sites for a greater occipital nerve block, including injection sites at one third the distance between the occipital protuberance and the mastoid process, at one half (the midpoint) the distance between the occipital protuberance and the mastoid process, and at a point 1-2 cm inferior to the midpoint. Voight, Crystal L. and Maurice O. Murphy. "Occipital Nerve Blocks in the Treatment of Headaches: Safety and Efficacy." *The Journal of Emergency Medicine* 48.1 (2015): 115-129, 122. Print. Thus, it is essential that an injection targeting device be adaptable to a specific patient in order to permit a practitioner to administer an injection at a site using the landmark(s) and location methodology that the practitioner is familiar and comfortable with.

In other cases, such as when a patient has known anatomical variations, the location of underlying structures and/or tissues may be determined for a specific a patient via established methods including, but not limited to, imaging methods such as ultrasound, computed tomography (CT), and magnetic resonance imaging (MRI), nerve stimulation such as motor evoked potential testing, and palpation and percussion techniques. In these cases, preferred injection sites can be defined for a specific patient, for example by defining a preferred injection site relative to multiple (two or more) anatomical landmarks, or by defining an injection site in terms of a distance and direction (in terms of degrees, watch face, etc.) relative to one anatomical landmark. Once preferred injection sites are established, they can be noted in a patient's medical records so that testing does not need to be repeated.

The present invention uses at least one anatomical landmark and known or established relationships relative to the at least one anatomical landmark to provide an injection site targeting device that facilitates consistent, reproducible administration of injections or other therapeutic means, such as nerve blocks, TENS, administration of medications, etc. across a variety of populations without requiring expensive diagnostic equipment. Additionally, because the injection site targeting device essentially serves as a template for the medical practitioner, the training necessary to administer a nerve block using the injection site targeting device can be reduced compared to the training required to administer nerve blocks using traditional anatomical landmark guidance techniques, imaging techniques, or nerve stimulation.

Further, while the invention is described as an injection targeting device, it should be appreciated that the devices described herein are applicable to any treatment or procedure that relies on reliable identification of the location of nerves in order to be effective. Transcutaneous electrical nerve stimulation (TENS), for example, requires that electrodes be placed on the surface of the skin in close proximity to specific nerves. Any of the devices described herein could be adapted to identify a site for application or to mark the skin for repeated or later application, without departing from the scope of the invention. Further, while a nerve block is typically administered by a medical practitioner, it should be appreciated that, in some contexts, such as TENS administration, the devices described herein are appropriate for use by a lay person, and may be used to facilitate self-administration of treatment by a patient for the administration of therapy at home or in a non-clinical setting. The devices described herein could also be used to place a radiofrequency probe or catheter introducer at a specific location on the body for treatment, diagnostics, or monitoring.

Figure 1B:
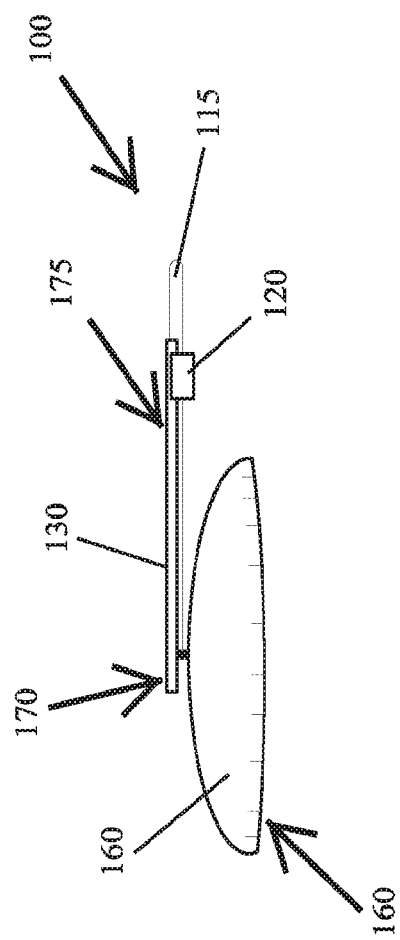

FIGS. 1A and 1B illustrate an injection site targeting device 100 in accordance with the present invention. The injection site targeting device 100 includes a landmark identifier 110, an adjustment mechanism 115 that includes a slider 120, a targeting band 130, a marker 140, a measurement guide 150, a directional guide 160, and a connector 170. The landmark identifier 110 is configured to be placed on or over an anatomical landmark that has been identified by a user. Landmark identifier 110 may be adapted in shape and size to suit, conform to, or accommodate the anatomical landmark it is intended to identify. For example, where the identified anatomical landmark is a bony landmark that protrudes from the body, such as the mastoid process, the occipital protuberance, the medial malleolus, or the lateral malleolus, the bottom of the landmark identifier may be concave or cupped to receive a bony projection, may be soft and moldable to conform to the bony landmark, or may include a partial depth hole or through hole that permits a user to identify the position of the landmark via visual inspection or palpation. A landmark identifier intended for use with the medial malleolus may be larger in diameter and have a deeper cup or concavity to its shape than a landmark identifier intended for the occipital protuberance. Where the chosen anatomical landmark does not protrude from the body, for example, in the case of soft tissue landmarks such as the edge of a facial feature such as an eyebrow, or underlying tissue that can be identified via palpation, the landmark identifier may have a flat bottom. In still other embodiments, landmarks may be identified via conventional imaging means and temporary, semi-permanent, or permanent marks can be made on a patient's skin to facilitate repetitive placement of a landmark identifier via visual inspection. In some cases, at least a portion of the landmark identifier may be inserted beneath the skin to facilitate identification of a specific landmark via physical inspection or palpation. Landmark identifier 110 may be constructed of any material, but are preferably conducted of a material or combination of materials that is unlikely to cause skin irritation. In some embodiments, it is preferable that the material or materials withstand chemical and/or heat sterilization procedures. Exemplary materials include, but are not limited to, polymers, including silicone polymers and plastics, and metals and metal alloys.

Landmark identifier 110 may be held in place by a person, secured to the skin via a skin adhesive such as a silicone adhesive, secured via an elastic band, hook and loop fastener, tape, or any other fastener, frame, or combination thereof that allows for landmark identifier 110 to be held securely against the patient's body and the anatomical landmark. It should also be appreciated that, in some embodiments, the landmark identifiers may be labeled or color coded to indicate the anatomical landmark intended to be used with that specific landmark identifier. In some embodiments, landmark identifier 110 includes a directional guide 160, indicating direction via, for example, degrees (360) or in terms of a clock face. In other embodiments, the landmark identifier may include an opening or port that allows a user to view and/or palpate an anatomical landmark to facilitate placement of the injection targeting device, or to view and/or palpate the anatomical landmark while the injection site targeting device is in place on a patient. Landmark identifier 110 may be constructed of any material suitable to be placed against a patient's skin, but is preferably a material unlikely to cause skin irritation on contact. In some embodiments, it is desirable for the material or combination of materials to be sterilizable. Exemplary materials include, but are not limited to, metals such as austenitic 316 stainless steel, martensitic 440 and 420 stainless steels, titanium alloys (such as Ti6Al4V), and the like, and polymers such as polypropylene, polytetrafluoroethylene, polyether ether ketone (PEEK), silicone, and the like.

The adjustment mechanism 115 is connected to landmark identifier 110 via connector 170. Connector 170 may be any fastener including, but not limited to, a pin, screw, nut, nut/bolt combination, clamp, adhesive, or any other fastener that can secure adjustment mechanism 115 to landmark identifier 110 permanently, temporarily, or removably. In some embodiments, the connector may be formed integrally with the landmark identifier and targeting band. In some embodiments, connector 170 permits the adjustment mechanism to pivot relative to the landmark identifier. Adjustment mechanism 115 includes slider 120, which is configured to move along the length of the adjustment mechanism 115. In some embodiments, slider 120 can be secured in a specific position, for example, by tightening connector 175. The length of adjustment mechanism 115 is such that it permits the slider to move at least the distance from the landmark locator to the desired injection site. Preferably the travel of the slider is greater than the distance from the landmark locator to the desired injection site. Further, the adjustment mechanism may be straight (flat), or curved to mimic the curvature of the part of the body on which it is to be used. The adjustment mechanism may be constructed of any material with sufficient structural characteristics to withstand manipulation and tension without deforming. In some embodiments, it is preferable that the adjustment mechanism be constructed of sterilizable metal or polymers, or a combination thereof, as discussed with respect to the landmark identifier.

Targeting band 130 is connected to the adjustment mechanism at two points, and should be under increasing tension as slider 120 is moved away from landmark identifier 110. At a first end, targeting band 130 is connected to the adjustment mechanism 115 and the landmark identifier 110 via connector 170 described above, or may be directly connected to adjustment mechanism 115. In some embodiments, the connection between the landmark identifier and the targeting band is a pivotable connection. At a second end, targeting band 130 is connected to slider 120 via connector 175. Connector 175 may be a pin, screw, bolt, nut/bolt combination, clamp, adhesive, or any other appropriate fastener or fixative to temporarily, permanently, or removably connect targeting band 130 with slider 120. In some implementations, the targeting band may be secured at the second end by fixing the targeting band between 2 portions of the slider.

Marker 140 is located on targeting band 130, and is used to indicate the preferred injection site. The marker 140 may be located at any point on the targeting band that will extend beyond the boundaries of the landmark identifier under tension. In some embodiments, specific points are marked along the band, such as ⅓, ⅔, or both ⅓ and ⅔. In other embodiments, multiple markers may be located on the targeting band to define a scale. Targeting band 130 is deformable so that the position of marker 140 can be adjusted by moving slider 120 until marker 140 is in the desired position, and then securing the slider to the adjustment mechanism via, for example, a thumb screw. Adjustment mechanism 115 optionally includes measurement guide 150, which may be a ruler or provide other consistent markings to indicate position relative to the identified anatomical landmark.

In the embodiment illustrated in FIGS. 1A and 1B, targeting band 130 may be constructed of any material that will deform in the axial direction under the tension created as the slider 120 is moved away from landmark identifier 110. Preferably, the material deforms linearly in the axial direction over a distance of at least a few millimeters to a few centimeters or more, depending on the distance from the landmark to the injection site, or the distance between the landmarks. In some embodiments, for example where the distance between landmarks is relatively large (50 or more centimeters), it is preferable that the material deforms linearly in the axial direction over at least a portion of the distance between the landmarks. For example, in dealing with nerves on the head the material should deform linearly in the axial direction when stretched 3-10 centimeters. This permits the same band to be used on patients of different shapes and sizes, and accounts for the variation in anatomical features that exist from person to person or patient to patient. When landmarks are more than a few centimeters apart, it may be preferable that only a portion of the targeting band immediately around the injection site be constructed of a material that deforms linearly in the axial direction, while the surrounding sections of the targeting band are constructed of a material the does undergoes minimal or no deformation in the axial direction. In some embodiments, for example, where only one adjustment is necessary, such as embodiments where the targeting band is intended to be disposable or for single use, plastic deformation of targeting band 130 is acceptable. A non-limiting example of a material that would undergo plastic deformation in this context is polyvinyl chloride (plastic wrap). In other embodiments, for example, where repeated adjustment may be necessary, or where the targeting band is to be reused, elastic deformation is preferable. A non-limiting example of a material that deforms linearly in this context is high purity silicone rubber.

Marker 140 indicates the desired injection site and may be a mark on the targeting band, a through hole, a through hole covered by a thin film, a scored mark or partial-depth hole configured to guide a needle and/or limit the depth to which a needle can be inserted, or a tapered or funnel-shaped opening configured to guide a needle on the superior or inferior surface, direct the trajectory of a need, and/or limit the depth to which a needle can be inserted. In some embodiments, marker 140 may be formed continuously as part of targeting band 130, for example, when targeting band 130 is formed via a molding process using high purity silicone rubber. In other embodiments, marker 140 may be formed of a different material, such as metal or plastic, that is inserted into an opening in targeting band 130 or fixed in targeting band 130 during the manufacturing process, forming an eyelet or tunnel in the targeting band. In some embodiments, a marker may be added by a user after manufacture, for example by piercing the targeting band at an appropriate point and inserting a metal or plastic marker, or by making a mark on the targeting band before use, for example, with a permanent marker.

The embodiment illustrated in FIGS. 1A and 1B is particularly useful in cases such as that described by Loukas, where the preferred injection site for a greater occipital nerve block is indicated as being 2 cm medial and 2 cm inferior to the occipital protuberance. Using basic geometry, the preferred injection site is approximately 2.83 cm from the occipital protuberance at about 270 degrees. In order to use the injection targeting device of FIGS. 1A and B, one would place the landmark identifier on a patient's occipital protuberance, orienting the direction guide in the same manner as a compass, adjust and fix the slider so that the marker is located 2.83 cm from the landmark identifier, and pivot the adjustment mechanism (and targeting band) so that the marker is located at 270 degrees using the direction guide.

Figure 2A:
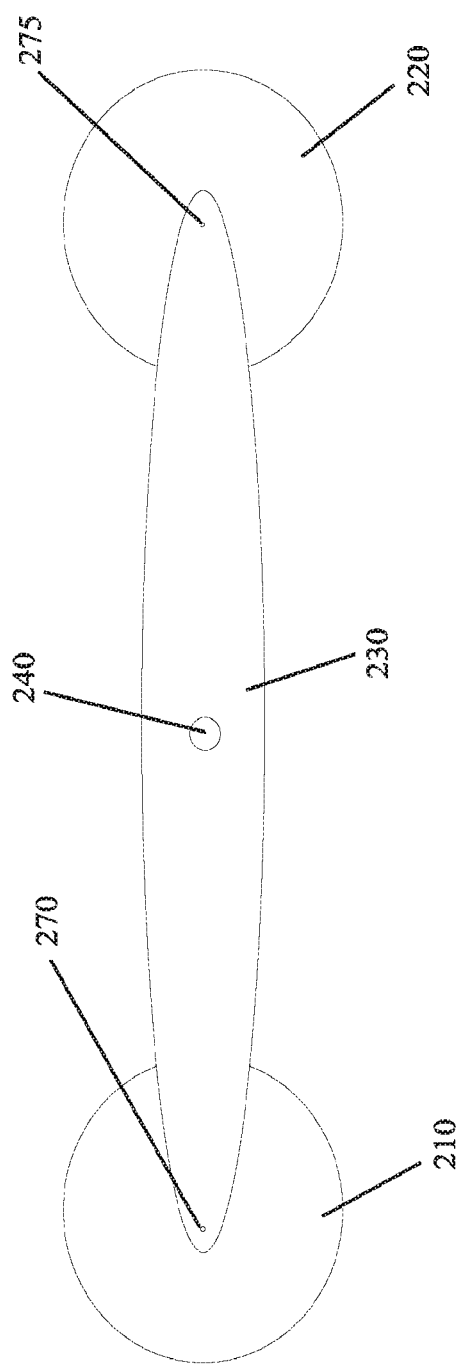
FIGS. 2A, 2B, 2C, 2D, 2E, 2F, 2G, 2H, 2I and 2J illustrate injection site targeting devices in accordance with the present invention.
Figure 2B:
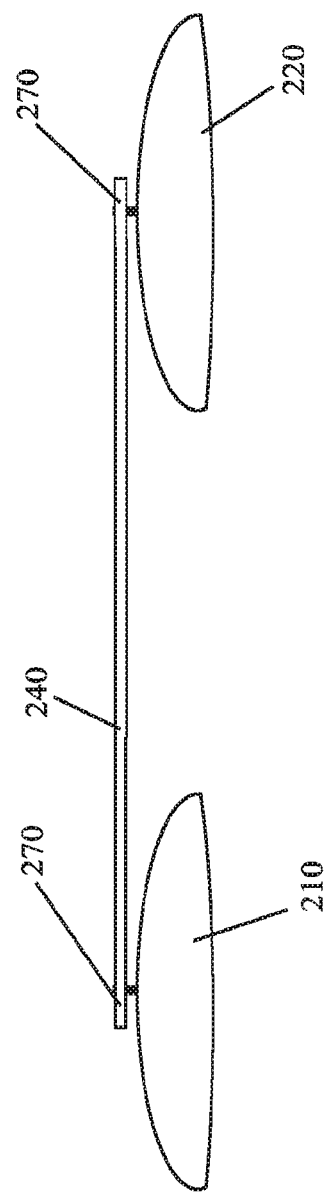

FIGS. 2A and 2B illustrates an injection site targeting device in accordance with the present invention. The injection site targeting device includes two landmark identifiers 210, 220, a targeting band 230, connectors 270 and 275, and a marker 240 to identify a preferred injection site. Each landmark identifier 210, 220 is configured to be placed on an anatomical landmark that has been identified by a medical professional or by a layperson. Landmark identifiers 210 and 220 may be adapted in shape and size to suit the landmark they are intended to identify without departing from the scope of the invention. For example, where the identified anatomical landmark is a bony landmark that protrudes from the body, such as the mastoid process, the occipital protuberance, the medial malleolus, or the lateral malleolus, the bottom of the landmark identifier may be concave or cupped to receive a bony projection, may be soft and moldable to conform to the bony landmark, or may include a partial depth hole or through hole to permit visual inspection and/or palpation by a user. A landmark identifier intended for use with the medial malleolus may be larger than a landmark identifier intended for the occipital protuberance. Where the chosen anatomical landmark does not protrude from the body, for example, in the case of soft tissue landmarks such as the edge of a facial feature such as an eyebrow, the landmark identifier may have a flat bottom.

Landmark identifiers 210 and 220 may be constructed of any material, but are preferably conducted of a material or combination of materials that is unlikely to cause skin irritation. In some embodiments, it is preferable that the material(s) can be sterilized. Exemplary types of materials include, but are not limited to, polymers, including plastics and silicone, and metals and metal alloys. Exemplary materials include, but are not limited to, metals such as austenitic 316 stainless steel, martensitic 440 and 420 stainless steels, titanium alloys (such as Ti6Al4V), and the like, silicone, and plastics such as polypropylene, polytetrafluoroethylene, polyether ether ketone (PEEK), and the like. Landmark identifiers 210 and 220 may be held in place by a person, secured via a skin adhesive such as a silicone adhesive, secured via an elastic band, hook and loop fastener, tape, deformable materials, or any other fastener, frame, or combination thereof that allows for landmark identifiers 210 and 220 to be held securely against the patient's skin and, in turn, the identified landmark. It should also be appreciated that, in some embodiments, the landmark identifiers may be labeled or color coded to indicate the anatomical landmark intended to be used with that specific landmark identifier.

Targeting band 230 is connected to the landmark identifiers 210, 220 via connectors 270, 275. Connectors include, but are not limited to, pins, adhesives, clamps, screws, nuts, nuts and bolts, and the like. In some embodiments, the landmark identifiers may be formed integrally with the targeting band. The connection between targeting band 230 and the landmark identifiers may be permanent or removable and may be pivotable/rotatable or fixed. Targeting band 230 may be constructed of any material that deforms linearly under slight tension. In some embodiments, the targeting band may be constructed of a material that undergoes linear elastic deformation under slight tension. Preferably, targeting band 230 is constructed of a material that undergoes linear deformation under slight tension. In some embodiments, targeting band 230 may undergo linear elastic deformation under slight tension.

In some embodiments, the targeting band is constructed of a material that has a type A durometer hardness of 50-80, a tensile strength of 1000-1500 psi, elongation of 300%-700%, tear strength of 100-400 ppi, and specific gravity of 1-1.4. Exemplary materials include, but are not limited to, medical grade silicone including high purity silicone rubber, polyurethane, urethane copolymers, and foamed silicone. In some embodiments, it is preferable that the targeting band be constructed of an auxetic material, which has a negative Poisson's ratio in addition to the aforementioned materials characteristics, meaning that the material becomes slightly thicker and, in some cases, more rigid when stretched. In some embodiments, it is preferable, that the targeting band be constructed of an elastomer (such as polyurethane or silicone materials) that has a durometer hardness of 50-70 Shore A, a tensile strength of 1100-1300 psi, elongation of 300-500%, tear strength of 200-300 ppi. The targeting band is preferably slightly shorter than the distance between the two landmarks (in average populations) so that, when properly positioned, the targeting band is under slight tension. In still other embodiments, the targeting band may be trimmed to a desired length by a user.

Marker 240 marks the preferred injection site on the targeting band, based on the relative relationship between the landmarks. The location of marker 240 is determined based on the location of the desired injection site (nerve) relative to two anatomical landmarks, for example 40% of the distance between landmark A and landmark B. Thus, the location of the marker 240 may be varied based on the desired injection site and its position relative to anatomical landmarks. In some embodiments, the marker is a dot or other symbol printed on the targeting band. In other embodiments, the marker is a through hole or partial-depth hole that is covered by a thin membrane or film that is configured to be punctured by a needle, for example to indicate that the targeting band is "new." In still other embodiments, marker 240 is a shaped opening that serves as a needle guide and may be configured to limit the depth of insertion of the needle by forming a physical barrier, and/or may be configured to guide the needle at a specific path or trajectory. As described with respect to the embodiment illustrated in FIGS. 1A and 1B, the marker may be formed of the same material as the targeting band via, for example, molding, or may be formed of another material entirely and inserted in the targeting band during or after manufacture. In still other embodiments, the marker may be a scale printed on the targeting band or series of holes in the targeting band at defined intervals. By providing relative measurements rather than a specific mark, a medical professional can use his or her knowledge to choose an appropriate injection site using the scale. Because the targeting band undergoes linear deformation under slight tension, marker 240 will move as the targeting band stretches. Thus, a marker located 40% between the two landmark identifiers will continue to remain at 40% as the landmark locators are moved apart and the targeting band is stretched. This linear deformation allows the injection targeting device to be used on patients of varying shapes and sizes with consistent and reproducible results.

Figure 2C:
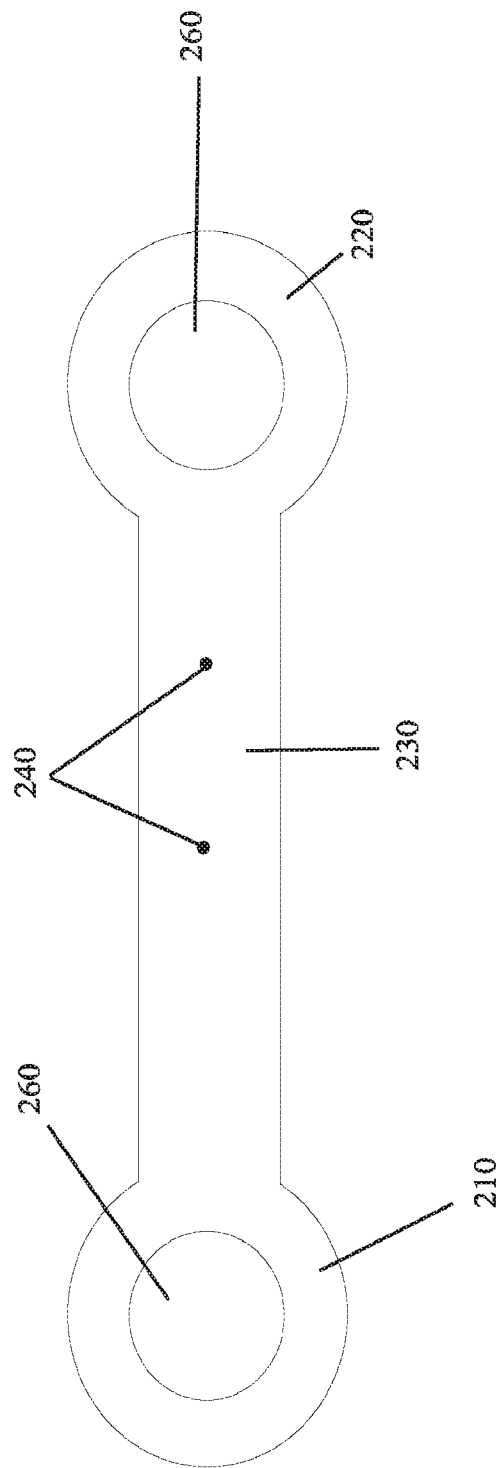
Figure 2D:
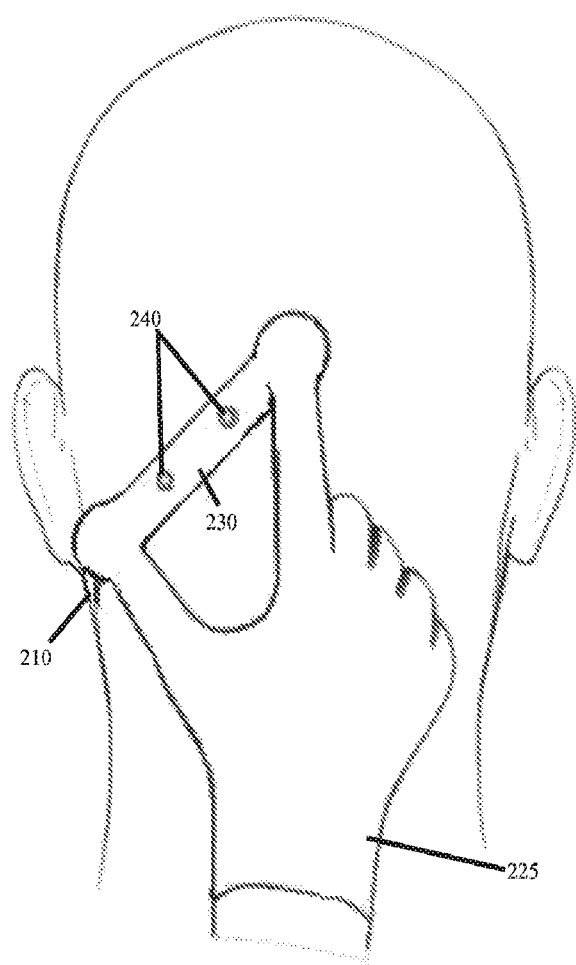

FIGS. 2C and 2D illustrate exemplary embodiments of injection targeting devices where the landmark identifiers 210 and 220 are formed integrally with the targeting band 230, and designed to be held in place using an adhesive and/or pressure applied by a practitioner, provider, the patient, or a third party. In FIG. 2C, landmark identifiers 210 and 220 include through holes configured to allow a user to inspect the patient's body, for example via visual inspection or manual palpation, in order to facilitate identification of the desired landmarks. FIG. 2D illustrates an embodiment similar to that illustrated in FIG. 2C, but includes integrated personal protective personal protective equipment (PPE) 225, in this case a glove, is connected with the landmark identifiers 210, 220 at 2 points. While the illustrated connection points to the landmark identifier is illustrated at the thumb and forefinger of the glove, it should be appreciated that the PPE may be connected at any points that will allow for the medical practitioner to properly locate the landmark identifiers while placing tension on the targeting band. The connection points may vary, for example, with the size of the glove. A glove designed for a larger hand may connect at the thumb and index finger, while a glove designed for a smaller hand may connect at the thumb and middle finger.

Figure 2E:
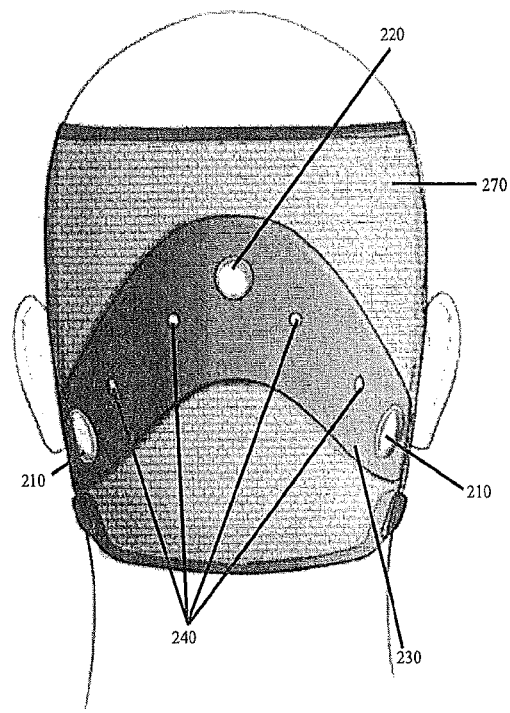
Figure 2F:
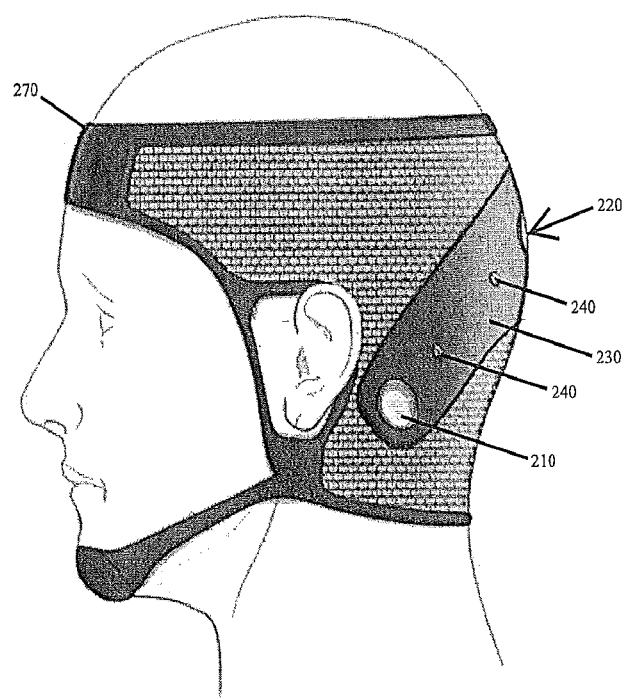

FIGS. 2E and 2F illustrate two different views of an exemplary embodiment of an injection targeting device configured to conform to the body of a patient. In the embodiment of FIGS. 2E and 2F, targeting band 230 has an inverted v-shape. Targeting band 230 includes multiple markers 240. Landmark identifiers 210 and 220 include through holes, and are formed integrally with targeting band 230. Targeting band 230 is attached to or embedded in a fastener 270, which is an elastic material that stretches and conforms to a patient's body to secure the landmark identifiers and, thus, markers in place on a patient. In some embodiments, the elastic material may be secured in place via hook and loop fasteners, snaps, buckles, or the like. In other embodiments, the elastic material may be self adhering material, such as 3M™ Coban™, that is secured by overlapping the material once it is wrapped around the body. Preferably, if the material is to be wrapped around the face or a joint, openings exist in the material to accommodate facial features, ears, and other anatomical features. The embodiment illustrated in FIGS. 2E and 2F also permits for simultaneous identification of multiple injection sites in the case where bilateral injection sites exist on the body.

Figure 2G:
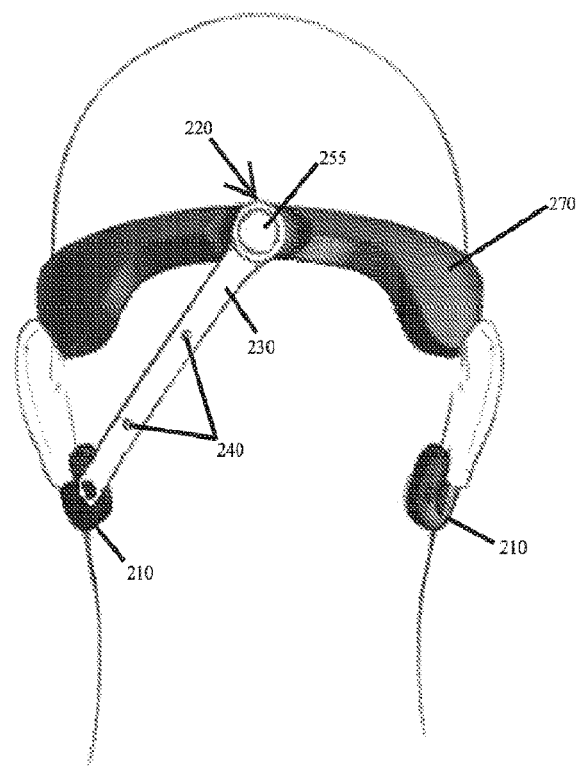
Figure 2H:
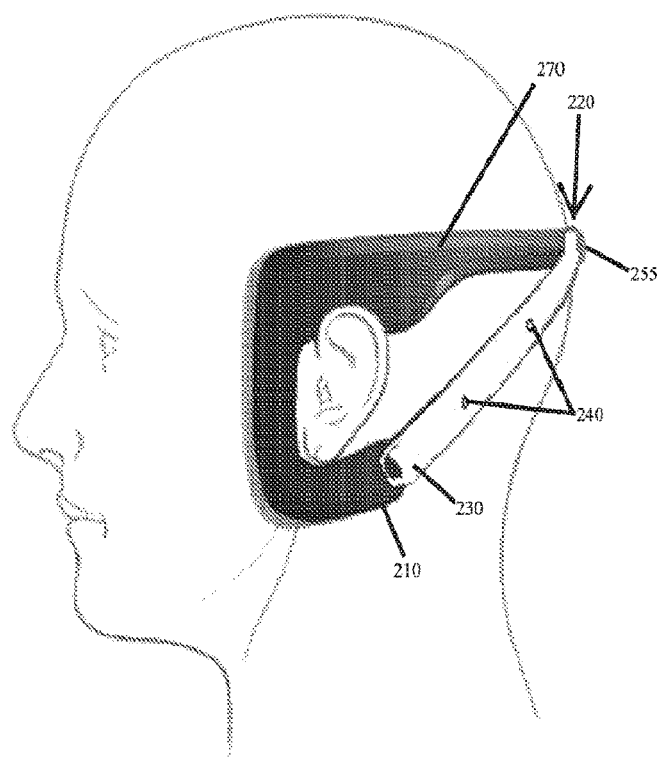

FIGS. 2G and 2H illustrate an exemplary implementation in which a frame is used to fix the targeting band to a patient. Specifically, the fastener 270 in this case is an adjustable frame that fits behind the head and over and around the ears of a patient, similar to "behind the head headphone" designs. Once the occipital protuberance 220 is located, the rear band of the frame can be adjusted to fit the head of the patient, for example via spring tension, sliding, or ratcheting mechanisms, or the like. The ends of the rear band are semi-rigid and are configured to be bent around the ears of the patient, in the reverse fashion of conventional eyeglasses. For example, the rear band of the frame extends over the top of a patient's ears, and down along the front of the ear, and each end of the band is bendable around the bottom of the patient's ears and back towards the mastoid process. The semi-rigid, bendable/deformable ends of the band also serve as landmark identifiers 210. Targeting band 230 is connected to the fastener 270 via a pivoting connection 255, which allows the targeting band to be secured to landmark identifier 210 on either side of the patient's head via a fastener, adhesive, or the like. Once targeting band 230 is secured to the second landmark identifier 210—identifying the mastoid process on either side of the patient—the targeting band 230 is under tension and the markers 240 can be used to identify injection sites. The rear band can be formed of a polymer, plastic, or metal. The semi-rigid (deformable) portions should retain the new shape once positioned, accordingly it is preferable that the semi-rigid portions be constructed of a deformable metal interior (wire) covered by foam, fabric, or other soft material that is unlikely to cause skin irritation, for patient comfort.

Figure 2I:
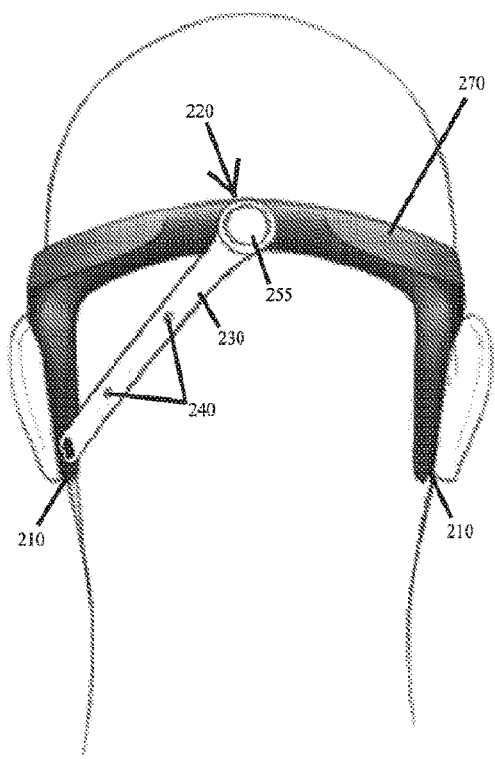
Figure 2J:
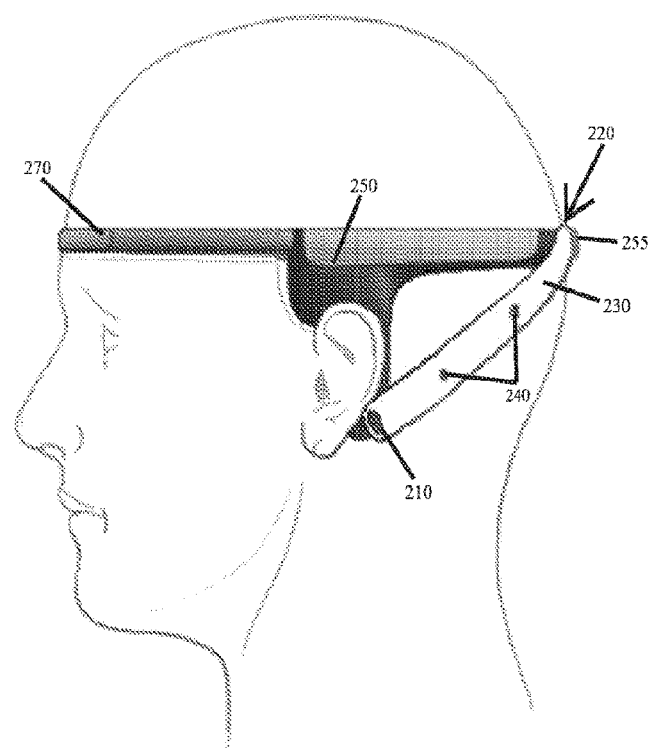

FIGS. 2I and 2J illustrate an exemplary implementation in which a combination of a frame and band used to fix the targeting band to a patient. In this embodiment, the fastener 250 is a an adjustable frame that fits behind the head and sits on top of a patient's ears. A band 270, such as an elastic band or hook and loop band, is configured to wrap around the front of a patient's head to further secure the frame. Once the occipital protuberance 220 is located, the rear band of the frame can be adjusted to fit the head of the patient, for example via spring tension, sliding, or ratcheting mechanisms, or the like. The ends of the rear band are semi-rigid and are configured to be bent along the back of a patient's ears, similar to the earpieces of conventional eyeglasses. The semirigid, bendable/deformable ends of the band also serve as landmark identifiers 210. Targeting band 230 is connected to the fastener 250 via a pivoting connection 255, which allows the targeting band to be secured to landmark identifier 210 on either side of the patient's head via a fastener, adhesive, or the like. Once targeting band 230 is secured to the second landmark identifier 210—identifying the mastoid process on either side of the patient—the targeting band 230 is under tension and the markers 240 can be used to identify injection sites. The rear band can be formed of a polymer, plastic, or metal. The semi-rigid (deformable) portions should retain the new shape once positioned, accordingly it is preferable that the semi-rigid portions be constructed of a deformable metal interior (wire) covered by foam or other soft material that is unlikely to cause skin irritation, for patient comfort.

To use the injection targeting device of FIGS. 2A through 2J, a medical professional locates the first anatomical landmark and fixes the first landmark identifier in place. The medical professional then fixes the second landmark identifier in place, using a fastening mechanism, and placing slight tension on the targeting band. The marker should then be in position to identify the preferred injection site so that a nerve block can be administered because the targeting band stretches linearly.

Figure 3:
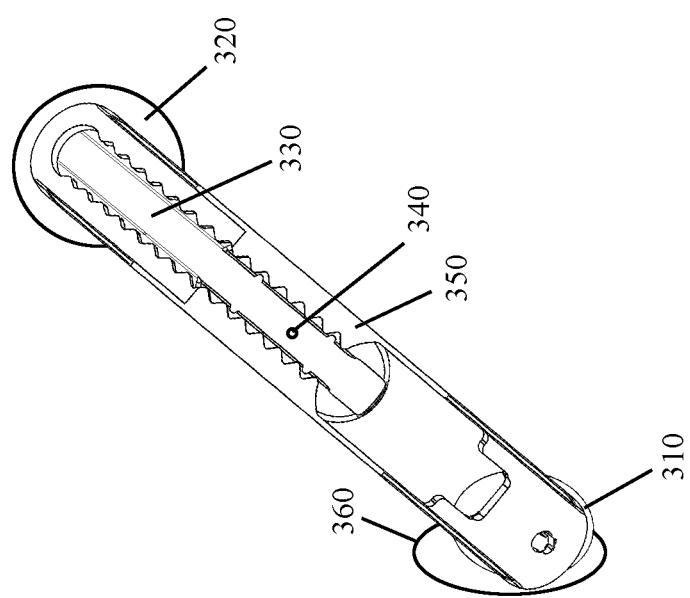
FIG. 3 illustrates an injection site targeting device in accordance with the present invention.

FIG. 3 illustrates an injection site targeting device in accordance with the present invention. In the embodiment illustrated in FIG. 3, the first landmark identifier 310 is configured to be anchored to a patient by elastic band 360. It should be appreciated, however, that any of the fixation mechanisms described herein may be used to anchor the injection site targeting device including, but not limited to, hook and loop fasteners, adhesive, a string, a headband, etc.

The first landmark identifier 310 and the second landmark identifier 320 are connected via a ratcheting tensioning member 350, and targeting band 330 is disposed within ratcheting tensioning member 350 such that the ratcheting tensioning member tensions the targeting band 330 as the position of the second landmark identifier 320 is adjusted. The tensioning mechanism may be constructed of materials such as those described with respect to the adjustment mechanism of FIGS. 1A and 1B, and the targeting band is preferably constructed of a material as described with respect to the embodiment illustrated in FIGS. 2A and 2B. While FIG. 3 illustrates a ratchet mechanism to adjust the length of the tensioning member, it should be appreciated that a variety of mechanical mechanisms could be used including, but not limited to, a cam mechanism, a slide, a threaded device, or the like could be used to adjust the tensioning member.

Figure 4:
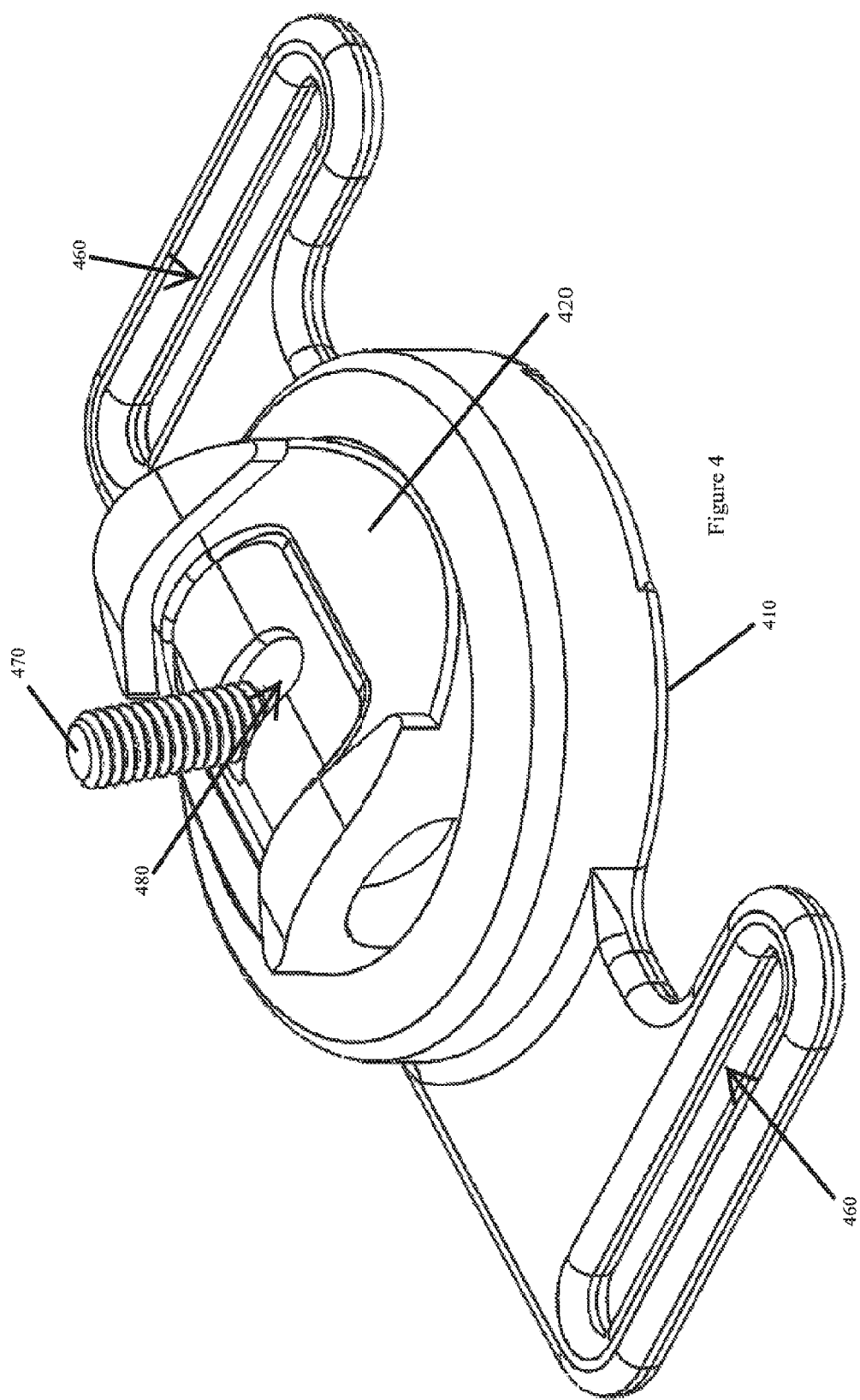
FIG. 4 illustrates a base component of an injection site targeting device in accordance with the present invention.

FIG. 4 illustrates a base component of an injection targeting device designed for the abortive and prophylactic treatment of headaches using occipital nerve blocks, which provides a pivotable connection to a pivot arm of an injection targeting device in accordance with the present invention. However, it should be appreciated that the design can be adapted to work with any injection site that can be defined by its position relative to an anatomical landmark. In the embodiment illustrated in FIG. 4, attachment points 460 include loops through which an elastic band, a ribbon or string, a cam or ratcheting strap, or a length of hook and loop fastener can be threaded to affix the device to a patient. It should be appreciated that the base component can be held in place using any of the means described herein. Landmark locator 410 is located at the bottom of the base component, and includes a concavity or depression to accommodate a patient's occipital protuberance. Threaded rod 470 protrudes from the base component through a slot 480 in rotary mount 420, and is pivotably connected to the base component, so that threaded rod 470 pivots in slot 480 in rotary mount 420. Pivot or rotary mount 420 allows for rotation of the threaded rod 470, so that threaded rod can pivot in the desired direction or orientation to accommodate curvature of a body part such as the skull. In some embodiments, it is preferable that the base component is comprised of metal or another material capable of withstanding sterilization, as described with respect to the embodiments in FIGS. 1A, 1B, 2A, and 2B.

Figure 5:
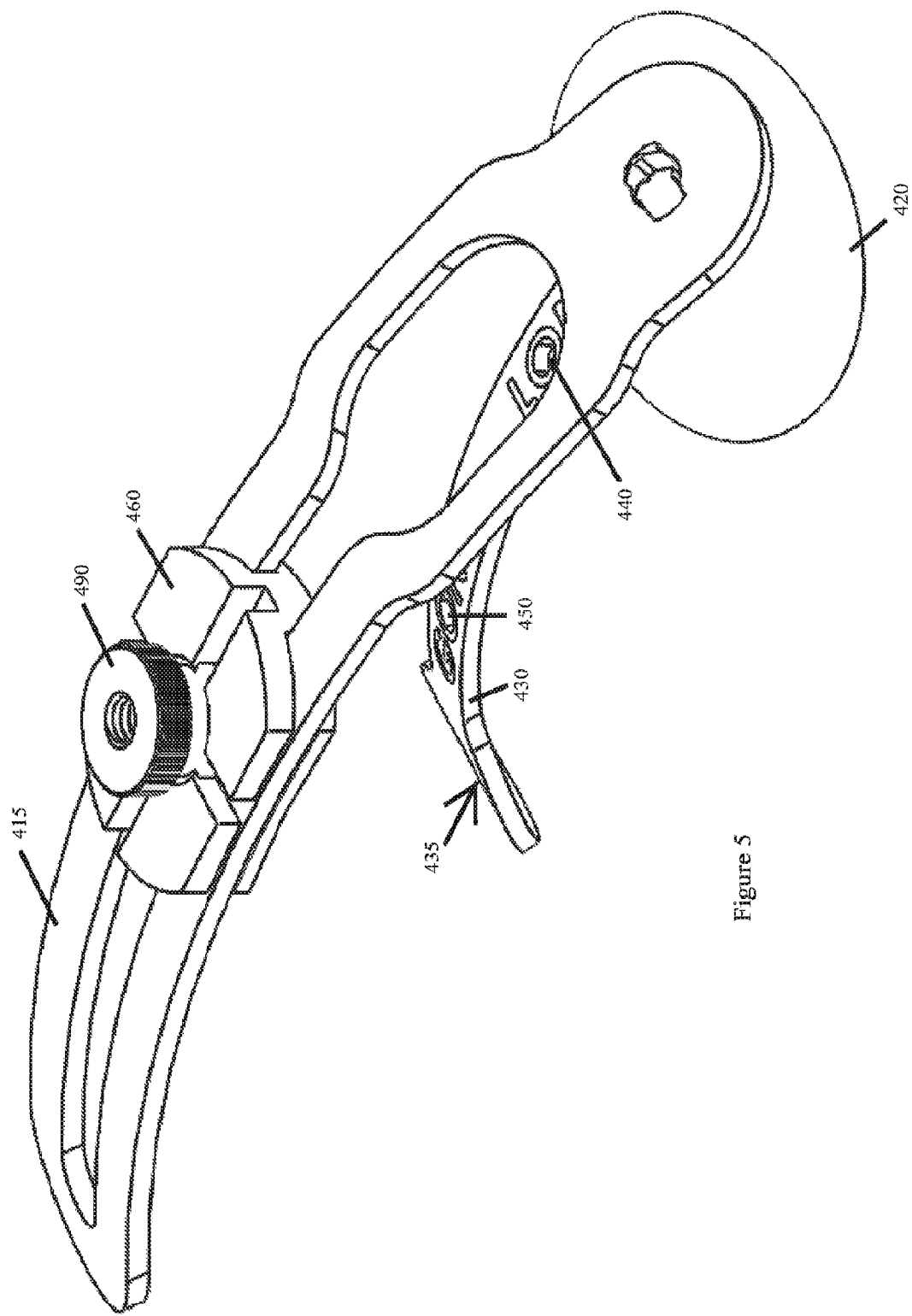
FIG. 5 illustrates a pivot arm of an injection site targeting device in accordance with the present invention.

FIG. 5 illustrates a pivot arm including a tensioning member and a targeting band in accordance with the present invention, for use with the base component illustrated in FIG. 4. Tensioning member 415 is a mechanical slide that is curved to accommodate the shape of a human head. As illustrated in FIG. 5, targeting band 430 is sandwiched between the tensioning member 415 and landmark locator 420 at first end. However, various configurations for the tensioning member are possible. For example, the tensioning member may extend from the side of the device, to facilitate manipulation of the tensioning member and minimize interference with the targeting band and injection site location. It should also be appreciated that the targeting band may be attached to the tensioning member using any conventional attachment mechanism. Targeting band 430 has a second attachment point 435 at its second end, which is configured to receive threaded pivoting rod 470. When the injection targeting device is completely assembled, threaded pivoting rod 470 extends through second attachment point 435 in targeting band 430 and through sliding retaining bracket 460. The base component/targeting band/sliding retaining bracket assembly is secured together via thumb nut 490. Sliding retaining bracket 460 slides within the slot of tensioning member 415 when tension applied via thumb nut 490 permits for adjustment. When sliding retaining bracket 460 is in the desired position, which preferably places landmark locators 410 and 420 over the desired anatomical landmarks, thumb nut 490 can be tightened to fix the injection targeting device in the appropriate position to administer an injection. It should be appreciated that the materials for the base member, tensioning member, landmark identifiers, and the targeting band have been described with respect to the embodiments illustrated in FIGS. 2A, 2B, and 3.

Figure 6:
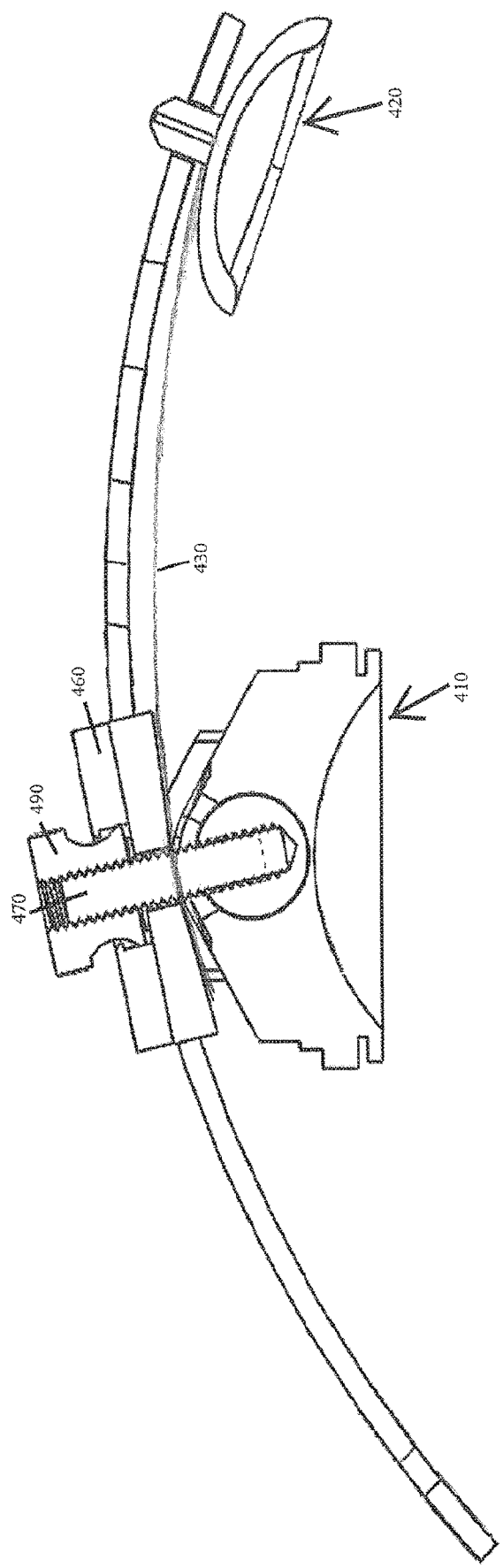
FIG. 6 illustrates a cross-section of an assembled injection site targeting device in accordance with the present invention.
Figure 7:
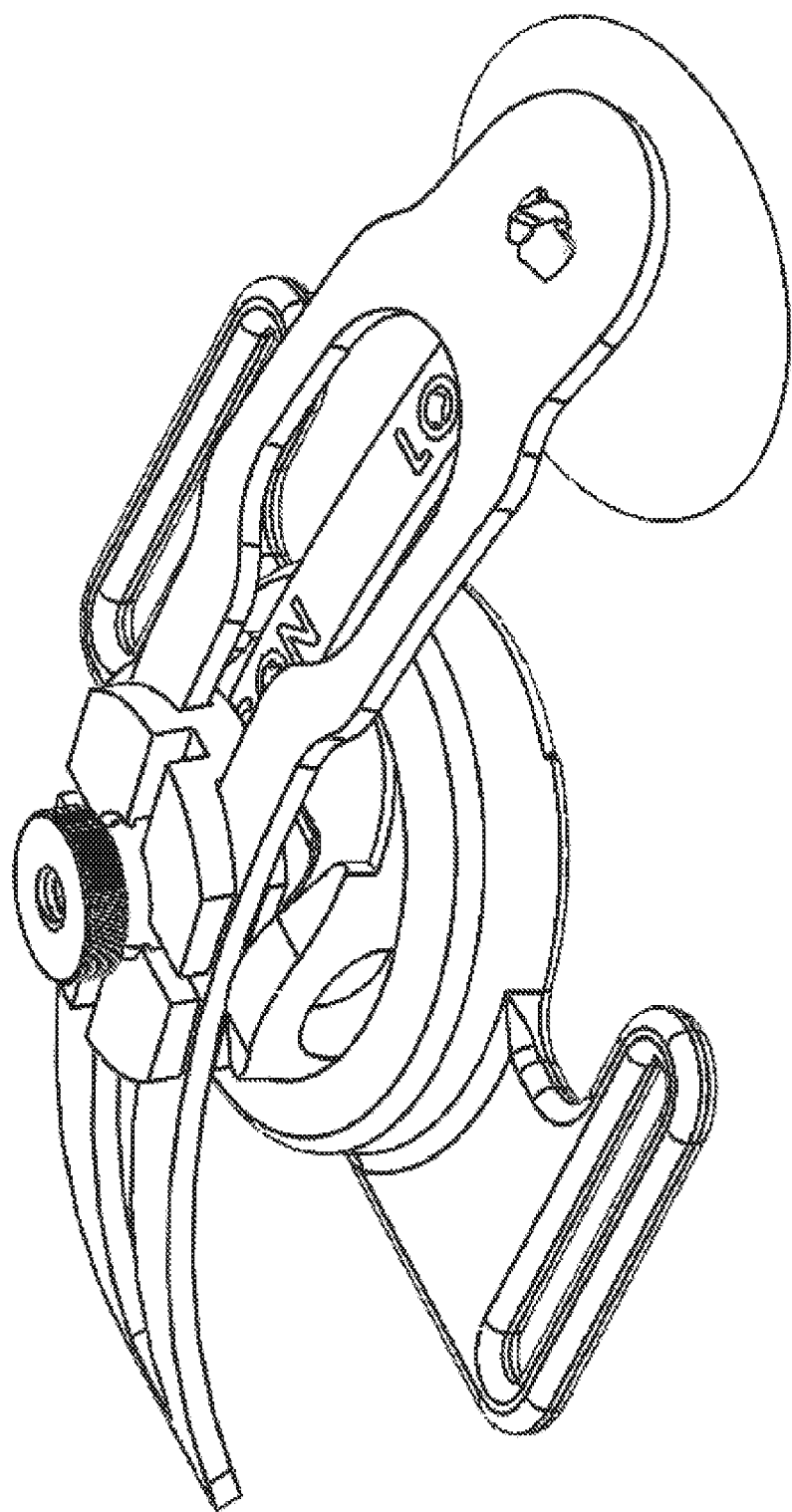
FIG. 7 illustrates an assembled injection site targeting device in accordance with the present invention.

Landmark locator 420 has a concave bottom configured to receive the mastoid process. Once landmark locator 420 is placed, thumb nut 490 is tightened to fix the retaining bracket 460 in position, placing tension on targeting band 430, which deforms linearly, as described with respect to the embodiment illustrated in FIGS. 2A and 2B, so that the marker remains in the same position relative to the landmark locators. The fully assembled injection targeting device is illustrated in FIGS. 6 and 7. Markers 440 and 450 identify the target injection sites for the lesser occipital nerve and greater occipital nerve, respectively. One known set of guidelines for locating an injection site for greater occipital nerve blocks and lesser occipital nerve blocks provides that the lesser occipital nerve is located one third the distance starting at the mastoid process and traveling in a line to the occipital protuberance, and the greater occipital nerve is located one third the distance starting at the occipital protuberance and traveling in line to the mastoid process. Thus, in the case of the greater occipital nerve and lesser occipital nerve, two injection sites can be targeted simultaneously with one device.

It should appreciated that the marker may be placed at any specified or desired point on the targeting band, and that multiple markers may be placed on the same band. In a non-limiting example, one occipital nerve block administration guideline suggests that a preferred injection is located at a distance of 20% to 23% from the occipital protuberance when traveling in line to the mastoid process. Thus, if this is a user's preferred guideline, a marker may be placed anywhere from 20% to 23% of the length of the targeting band, for example, a marker may be placed at 22% for this use.

Figure 8A:
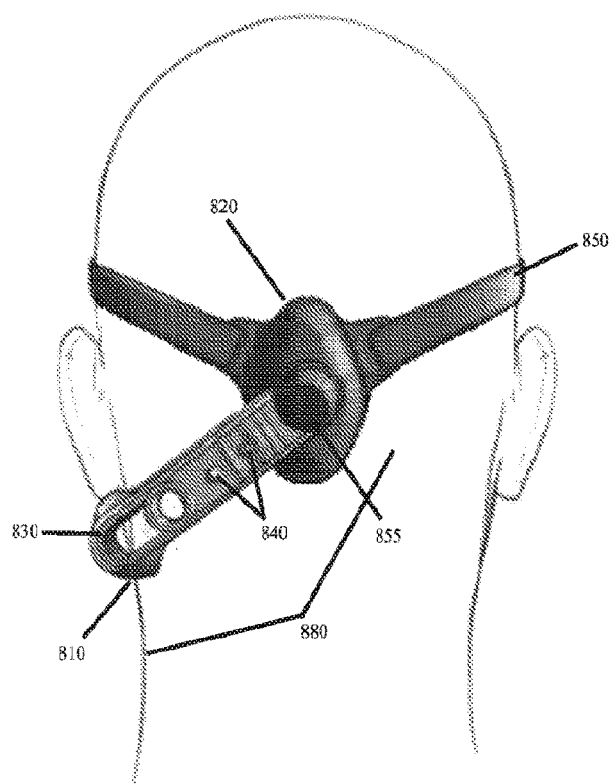
FIGS. 8A and 8B illustrate an injection site targeting device having a locking pivot arm, in accordance with the present invention.
Figure 8B:
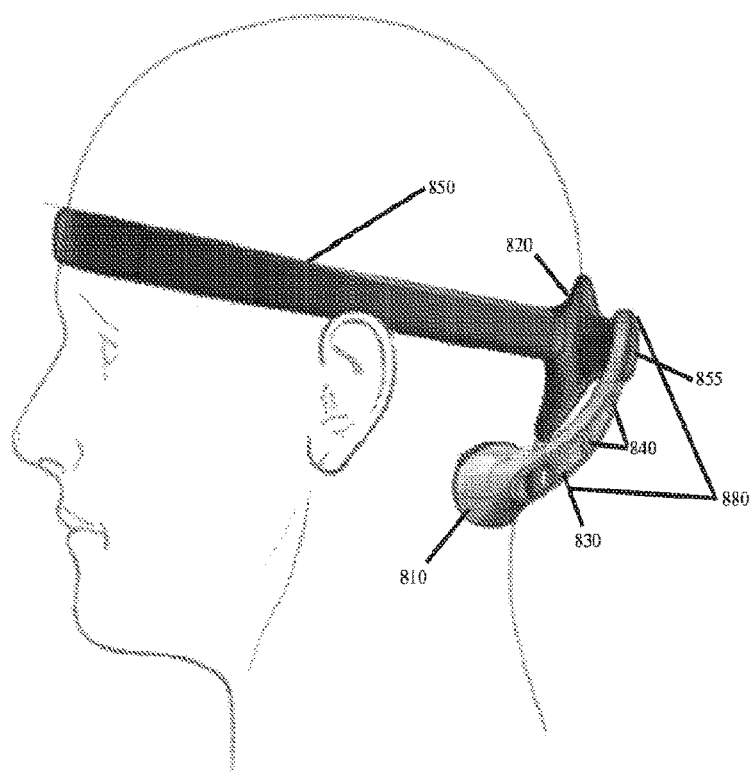

FIGS. 8A and 8B illustrate an injection site targeting device having a locking pivot arm, in accordance with the present invention including a linearly deformable targeting band. In the embodiment of FIGS. 8A and 8B, landmark identifier 820 is fastened to a landmark (in this case, the occipital protuberance) on a patient via a headband 850 constructed of elastic material, hook and loop fastener, or headband design that permits for adjustability in sizing. The pivot arm 880 is attached to landmark identifier 820 via a pivotable connection 855. Pivotable connections include all pivot joints, including friction lock pivot joints, tension pivot joints, sliding pivot joints, combinations thereof, and the like. In the embodiment illustrated in FIGS. 8A and 8B, the connection is also slidable, permitting manipulation of the pivot arm 880 by a user so that landmark identifier 810 can be placed on desired landmark (in this case the mastoid process). Any of a variety of mechanical locking mechanisms, such as a push button locking/unlocking mechanism, adjustable tension, or combinations thereof, may be used to permit manipulation of the pivot arm and/or lock the pivot arm in place. Targeting band 830, including markers 840, is fixed to the pivot arm at landmark identifier 810, and at pivotable connection 855. Thus, targeting band 830 deforms as pivot arm 880 is manipulated.

Figure 9A:
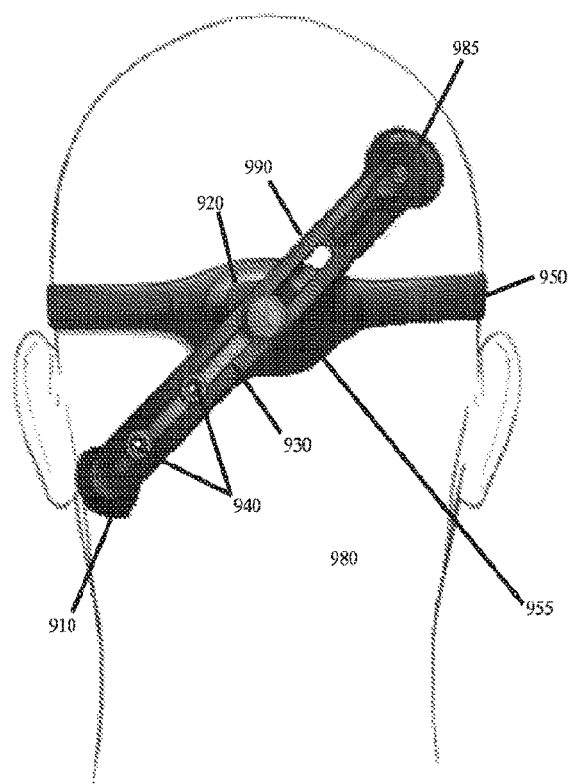
FIGS. 9A and 9B illustrate an injection site targeting device having a pivot arm with a track and additional support, in accordance with the present invention.
Figure 9B:
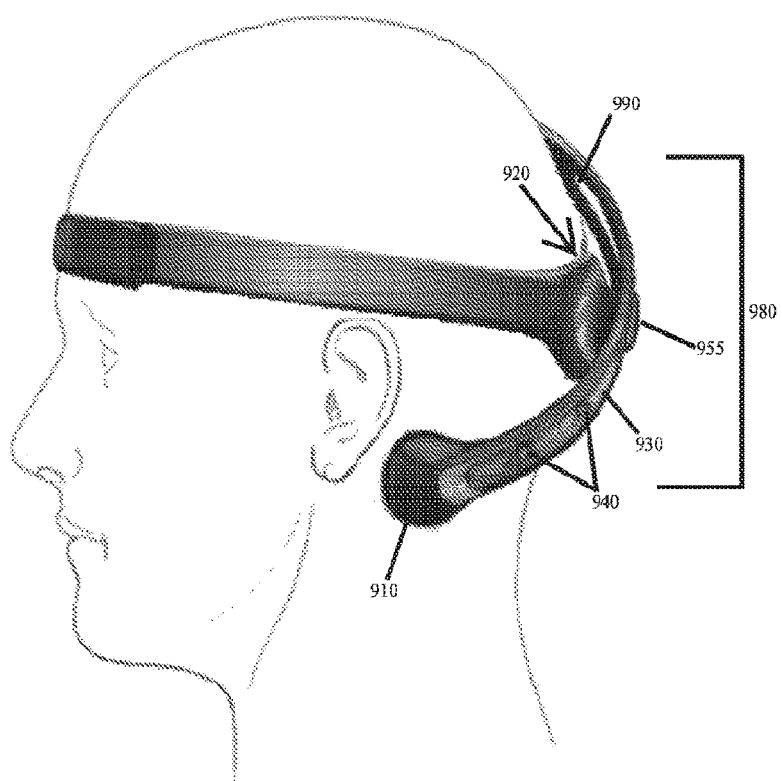

FIGS. 9A and 9B illustrate an injection site targeting device having a pivot arm with a track and additional support, in accordance with the present invention invention including a linearly deformable targeting band. In the embodiment of FIGS. 9A and 9B, landmark identifier 920 is fastened to a landmark (in this case, the occipital protuberance) on a patient via a headband 950 constructed of elastic material, hook and loop fastener, or headband design that permits for adjustability in sizing. The pivot arm 980 is attached to landmark identifier 920 via a pivotable connection 955. Pivotable connections include all pivot joints, including friction lock pivot joints, tension pivot joints, sliding pivot joints, combinations thereof, and the like. In the embodiment illustrated in FIGS. 9A and 9B, the connection is also slidable, permitting manipulation of the pivot arm 980 by a user so that landmark identifier 910 can be placed on desired landmark (in this case the mastoid process). Any of a variety of mechanical locking mechanisms, such as a push button locking/unlocking mechanism, adjustable tension, or combinations thereof, may be used to permit manipulation of the pivot arm and/or lock the pivot arm in place. The embodiment illustrated in FIGS. 9A and 9B also includes a support 985, which is designed to provide additional support and stability for pivot arm 980 during the injection process.

In the embodiment of FIGS. 9A and 9B, targeting band 930, including markers 940, is fixed to the pivot arm at landmark identifier 810, and at pivotable connection 855. Markers 940 include needle guides or eyelets, which provide structure for the markers. Pivot arm 980 includes a track 990, which slidably guide the needle guides as targeting band 930 deforms linearly.

Figure 10A:
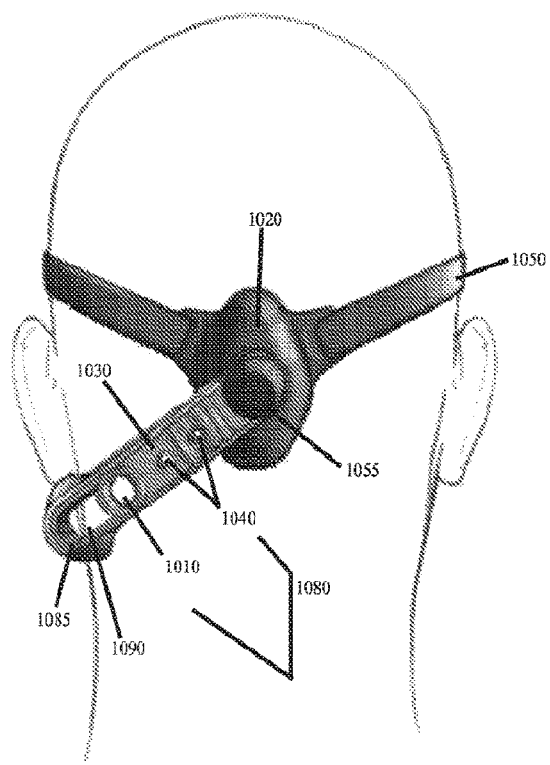
FIGS. 10A and 10B illustrate an injection site targeting device having a pivot arm with a track, additional support, and configured to locate a landmark via manual palpation, in accordance with the present invention.
Figure 10B:
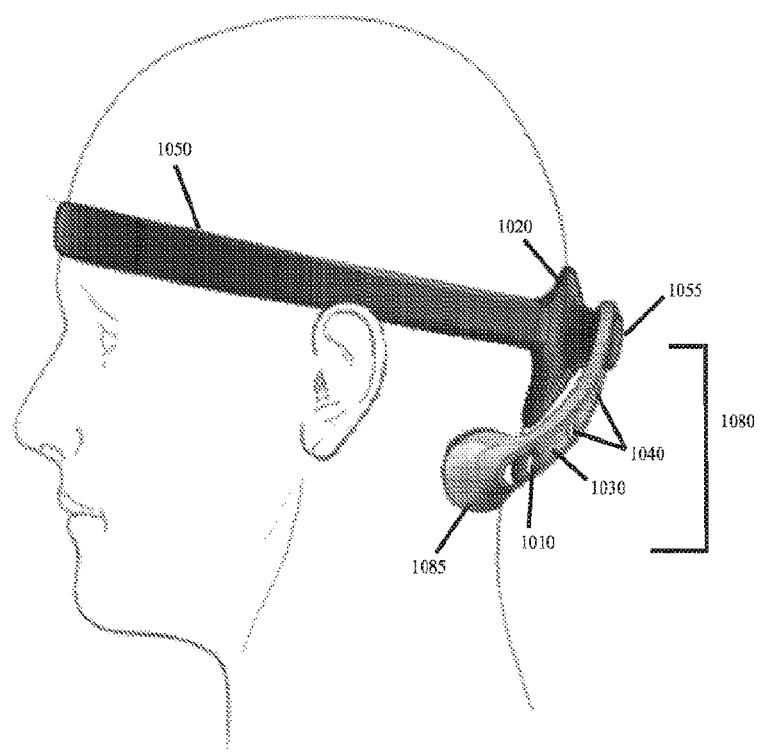

FIGS. 10A and 10B illustrate an injection site targeting device having linearly deformable targeting band and a pivot arm with a track, additional support, and configured to locate a landmark via manual palpation, in accordance with the present invention. In the embodiment of FIGS. 10A and 10B, landmark identifier 1020 is fastened to a landmark (in this case, the occipital protuberance) on a patient via a headband 1050 constructed of elastic material, hook and loop fastener, or headband design that permits for adjustability in sizing. The pivot arm 1080 is attached to landmark identifier 1020 via a pivotable connection 1055. Pivotable connections include all pivot joints, including friction lock pivot joints, tension pivot joints, sliding pivot joints, combinations thereof, and the like. In the embodiment of FIGS. 10A and 10B, landmark identifier 1010 is a through hole in targeting band 1030. In some embodiments, the through hole may be reinforced with a rigid material such as a metal or plastic insert. Any of a variety of mechanical locking mechanisms, such as a push button locking/unlocking mechanism, adjustable tension, or combinations thereof, may be used to permit manipulation of the pivot arm and/or lock the pivot arm in place. Targeting band 1030, including markers 1040, is configured to slide or be stretched along a slot or track 1090 in pivot arm 1080. In some embodiments, the position of targeting band 1030 and markers 1040 is secured by the user placing his or her finger on the landmark through the hole 1010. In other embodiments, targeting band 1030 slides along a track that includes a fixation mechanism that squeezes or clamps the band in place once the second landmark is located, fixing the targeting band in place and maintain tension on the targeting band. In still other embodiments, the position of the targeting band in the track may be manipulated via a ratchet mechanism. Support 1085 at the free end of the pivot arm provides support for the injection targeting device when in use.

It should be understood that, while examples are provided for targeting the greater and lesser occipital nerves, the targeting device disclosed herein can be applied to consistently target any location on the body that has a location that can be described relative to one landmark with a distance and relative direction, or that can be described relative to two landmarks, without departing from the scope of the invention. All figures included herein should be interpreted as illustrative of non-limiting, exemplary embodiments, and not in a limiting sense.

What is claimed is:

1. An apparatus for targeting an injection site using anatomical landmarks, comprising:
   a first landmark identifier;
   a second landmark identifier; and
   a targeting band connected with the first landmark identifier at a first end and the second landmark identifier at a second end, wherein at least a portion of said targeting band is linearly deformable in an axial direction under slight tension, the targeting band further comprising a marker identifying the injection site on the targeting band,
   wherein the marker comprises a needle guide.

2. An apparatus according to claim 1, wherein the first landmark identifier, second landmark identifier, and targeting band are formed integrally.

3. An apparatus according to claim 1, further comprising a tensioning member connected to the first and second landmark identifiers and configured to maintain tension on the targeting band after the first and second landmark identifiers are positioned on landmarks.

4. An apparatus according to claim 3, wherein the tensioning member is pivotably connected to one of the first and second landmark identifiers.

5. An apparatus according to claim 3, wherein the tensioning member is a mechanical slide.

6. An apparatus according to claim 3, further comprising a fastener connected with one of the first and second landmark identifiers, said fastener being configured to fix the position of the apparatus on a head of the patient.

7. An apparatus according to claim 6 wherein the first landmark identifier is connected with the fastener, and the tensioning member extends between the second landmark identifier and the fastener.

8. An apparatus according to claim 7, wherein the fastener is a headband.

9. An apparatus according to claim 1, wherein the targeting band includes at least a portion that is non-deformable under small amounts of tension.

10. An apparatus according to claim 1, wherein the marker is through hole in the non-deformable portion of the targeting band.

11. An apparatus according to claim 1, wherein the marker is on the linearly deformable portion of the targeting band.

12. An apparatus according to claim 1, wherein the targeting band is constructed of a material that has a negative Poisson's ratio.

13. An apparatus for targeting an injection site using anatomical landmarks on a patient, comprising:
   a targeting band having a first end and a second end, at least a portion of the targeting being linearly deformable, the targeting band comprising a marker identifying the injection site;
   a first landmark identifier pivotably connected to the targeting band at the first end;

a second landmark identifier configured to be connected with the second end of the targeting band; and a fastener configured to secure the first and second landmark identifiers to the patient.

14. An apparatus according to claim 13, wherein the targeting band includes at least a portion that is non-deformable under small amounts of tension.

15. An apparatus according to claim 13, wherein the marker is on the linearly deformable portion of the targeting band.

16. An apparatus according to claim 13, wherein the marker comprises a needle guide.

17. An apparatus according to claim 13, wherein at least a portion of the targeting band is constructed of a material that has a negative Poisson's ratio.

18. An apparatus according to claim 13, wherein the fastener is a headband.

19. An apparatus for targeting an injection site using anatomical landmarks, comprising:

a first landmark identifier;

a second landmark identifier; and a targeting band connected with the first landmark identifier at a first end and the second landmark identifier at a second end, wherein at least a portion of said targeting band is linearly deformable in an axial direction under slight tension, the targeting band further comprising a marker identifying the injection site on the targeting band;

a fastener connected with the first landmark identifier, said fastener being configured to fix the position of the apparatus on a head of the patient;

a tensioning member connected to the second landmark identifier and configured to maintain tension on the targeting band after the first and second landmark identifiers are positioned on landmarks, wherein the tensioning member extends between the second landmark identifier and the fastener.

20. An apparatus according to claim 19, wherein the fastener is a headband.

* * * * *